United States Patent
Srinivasan et al.

[11] Patent Number: 6,077,434
[45] Date of Patent: Jun. 20, 2000

[54] CURRENT-EFFICIENT SUPPRESSORS AND METHOD OF USE

[75] Inventors: Kannan Srinivasan, Sunnyvale; Victor Berber Barreto, Campbell; Christopher A. Pohl, Union City; James R. Thayer, Santa Clara; Neboisa Avdalovic, San Jose, all of Calif.

[73] Assignee: Dionex Corporation, Sunnyvale, Calif.

[21] Appl. No.: 09/232,116

[22] Filed: Jan. 15, 1999

[51] Int. Cl.⁷ .................................................. B01D 15/08
[52] U.S. Cl. ........................ 210/635; 210/638; 210/656; 210/659; 210/198.2; 204/520; 204/542
[58] Field of Search .................................. 210/635, 638, 210/656, 659, 644, 748, 198.2, 243; 204/518, 520, 522, 523, 524, 542, 536, 539, 630, 632, 638, 639; 436/150, 161, 175

[56] References Cited

U.S. PATENT DOCUMENTS

| | | |
|---|---|---|
| 3,897,213 | 7/1975 | Stevens et al. ......................... 210/656 |
| 3,920,397 | 11/1975 | Small et al. ............................. 210/284 |
| 3,925,019 | 12/1975 | Small Hamish et al. .............. 210/284 |
| 3,926,559 | 12/1975 | Stevens ................................... 210/284 |
| 4,403,039 | 9/1983 | Ban et al. ............................. 210/198.2 |
| 4,459,357 | 7/1984 | Jansen et al. ........................... 210/656 |
| 4,474,664 | 10/1984 | Stevens et al. ......................... 210/656 |
| 4,751,004 | 6/1988 | Stevens et al. ......................... 210/659 |
| 4,999,098 | 3/1991 | Pohl et al. .............................. 204/301 |
| 5,045,204 | 9/1991 | Dasgupta et al. ....................... 210/635 |
| 5,248,426 | 9/1993 | Stillian et al. .......................... 210/635 |
| 5,518,622 | 5/1996 | Stillian ................................. 210/198.2 |
| 5,597,481 | 1/1997 | Stillian et al. ....................... 210/198.2 |

Primary Examiner—Ernest G. Therkorn
Attorney, Agent, or Firm—Flehr Hohbach Test Albritton & Herbert LLP; David J. Brezner

[57] ABSTRACT

A method and apparatus for increasing the current efficiency of suppressor and suppress-like pretreatment devices is disclosed for the purpose of suppressing a high concentration of eluent without the detrimental effects of excess heat generation. The method and apparatus may be used in ion chromatography.

17 Claims, 8 Drawing Sheets

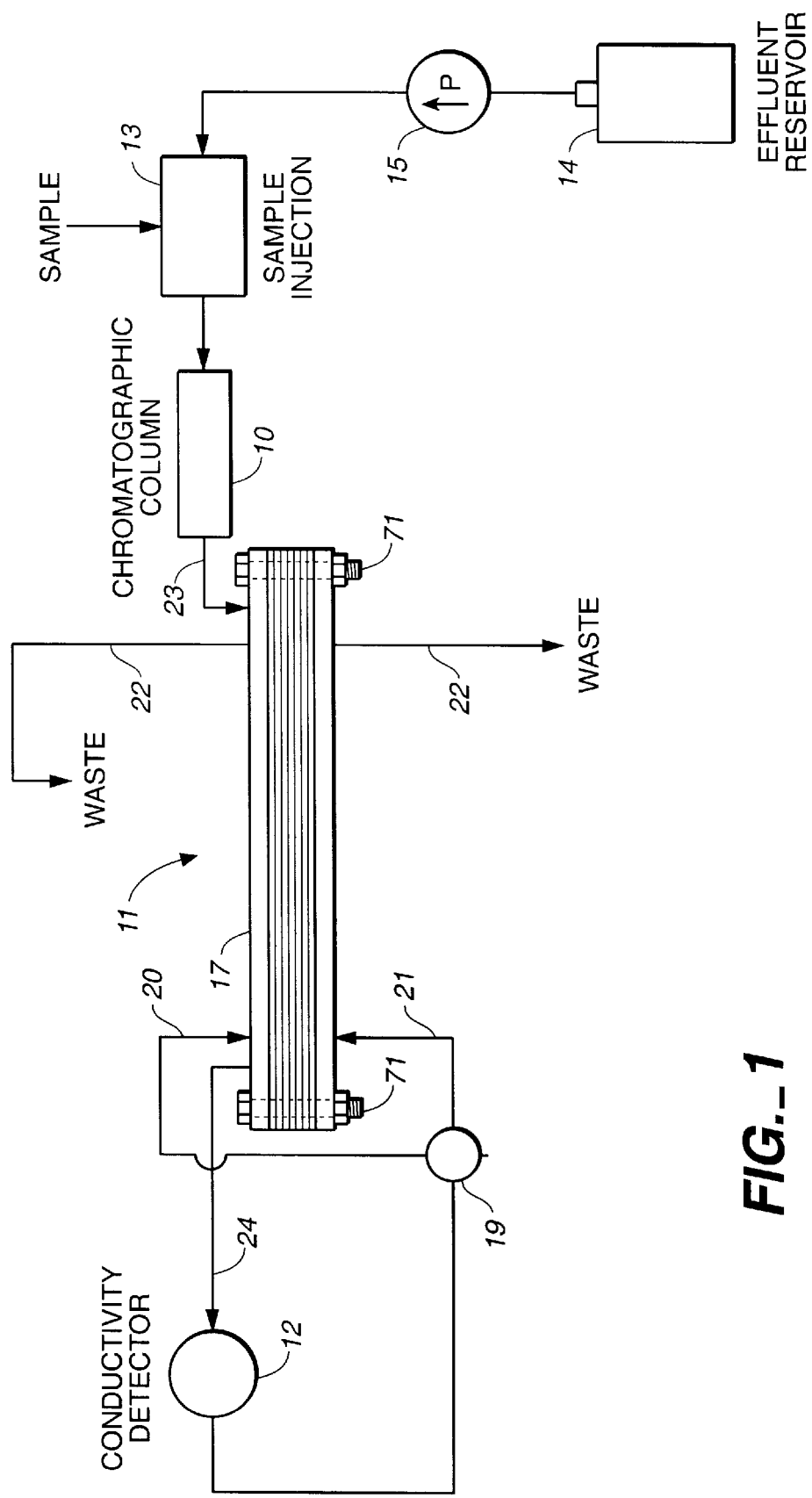
FIG._1

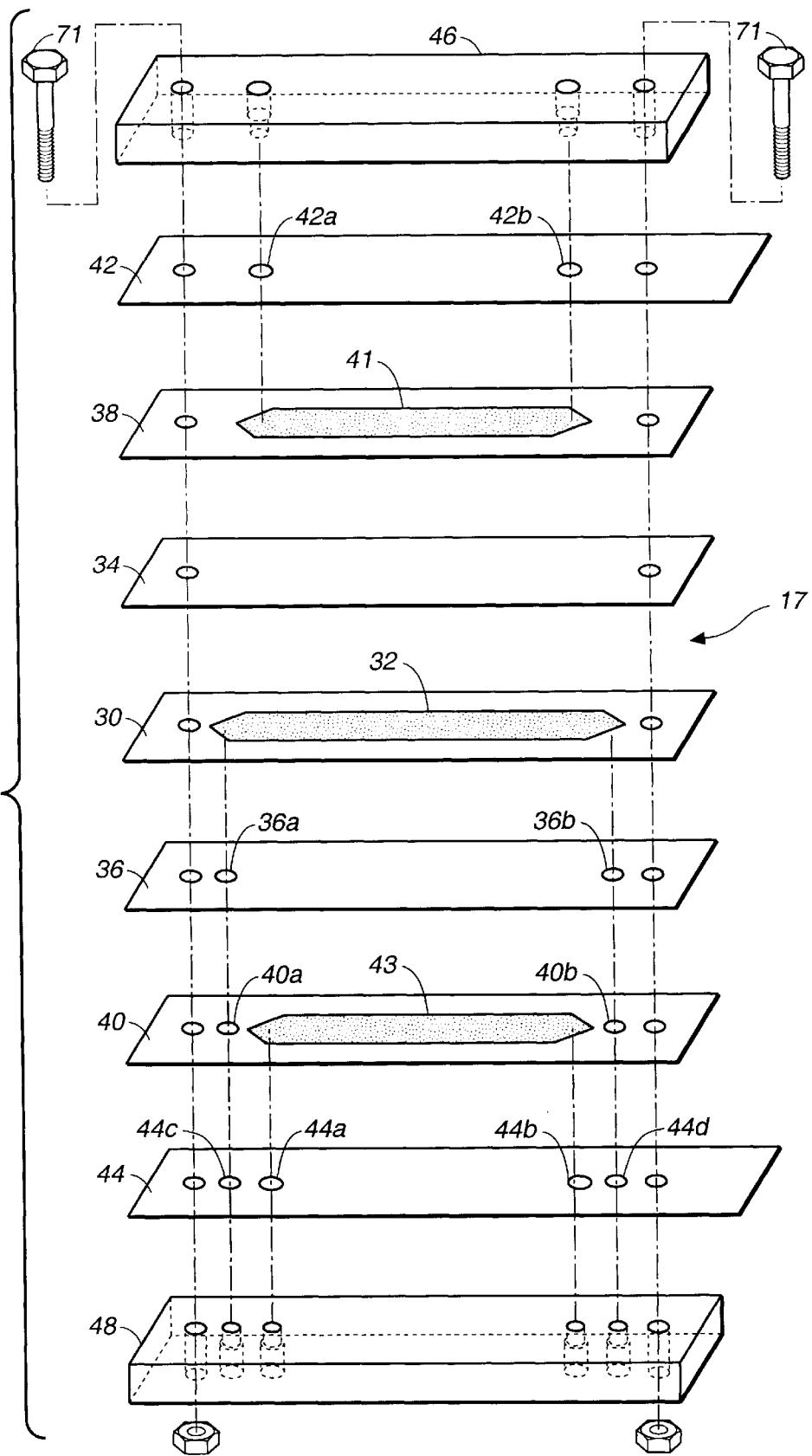
FIG._2

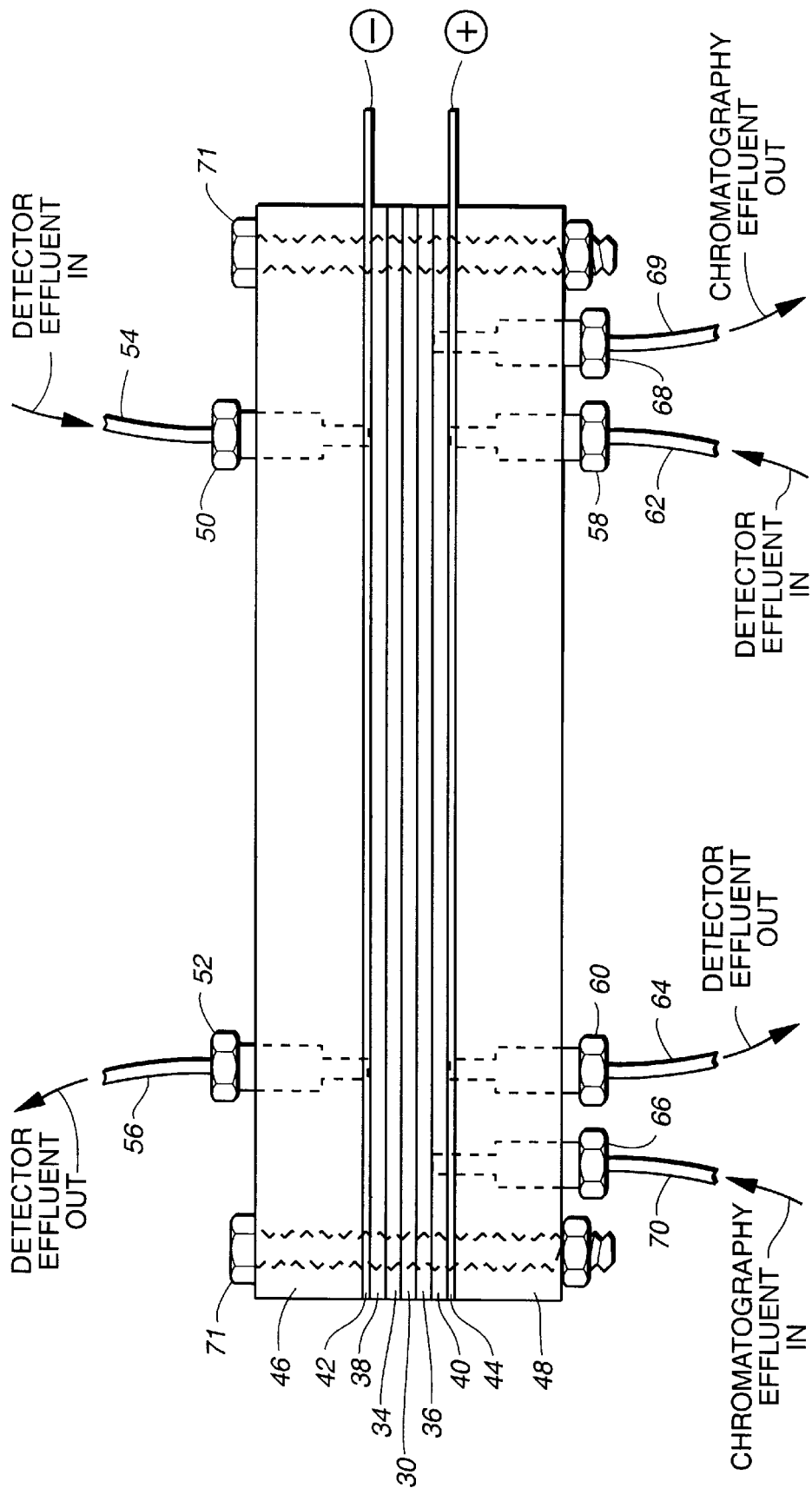
FIG._3

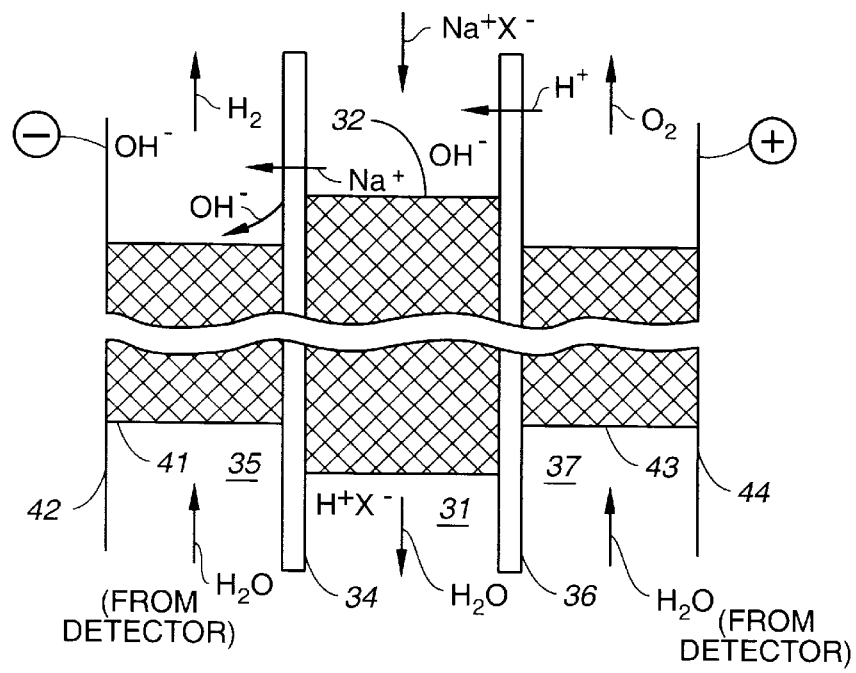
FIG._4
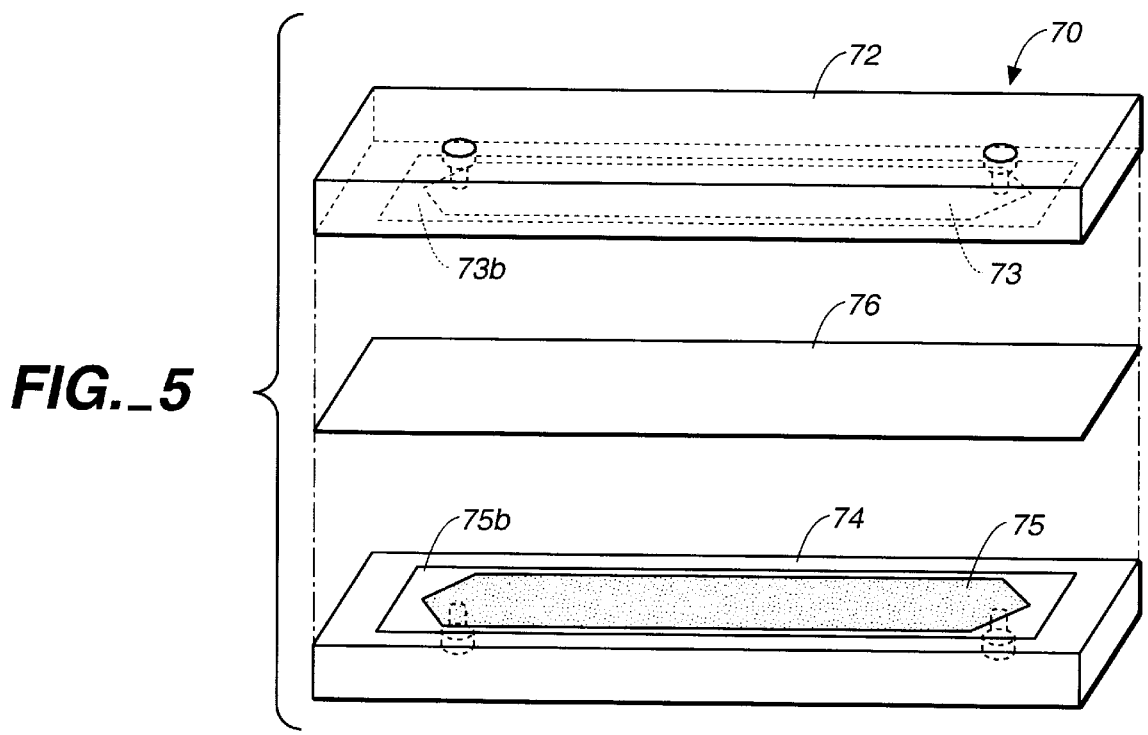
FIG._5

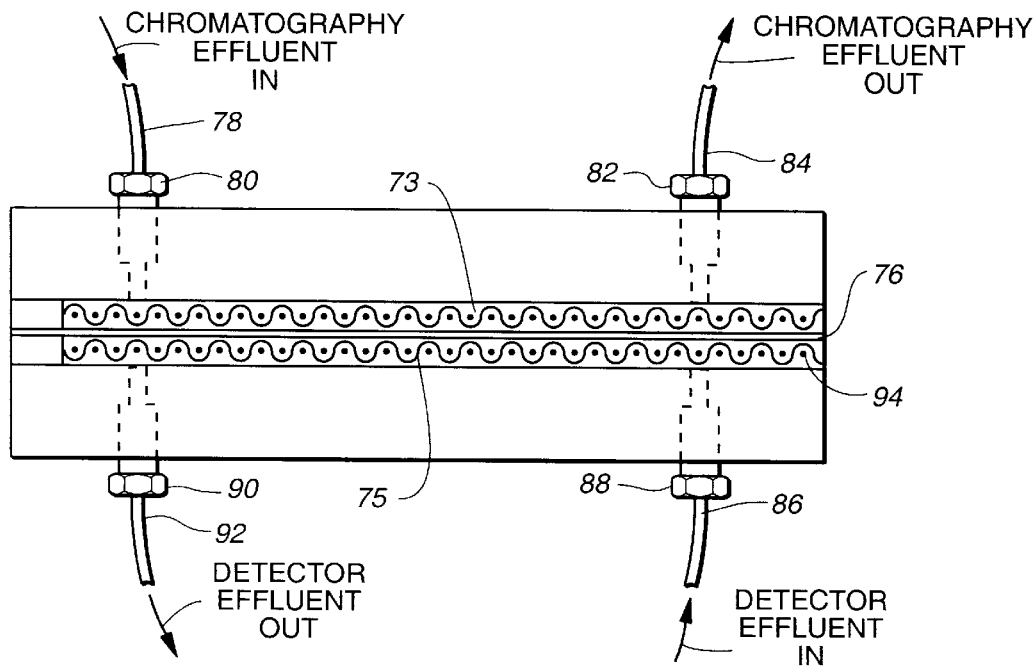
FIG._6
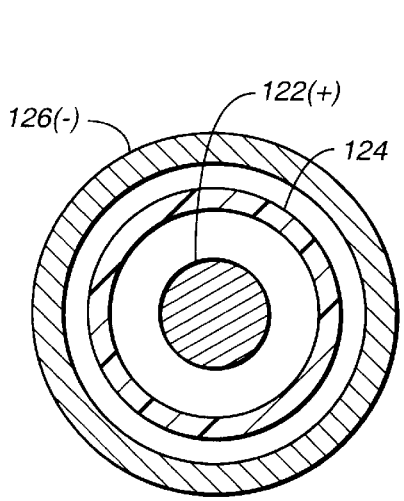
FIG._7
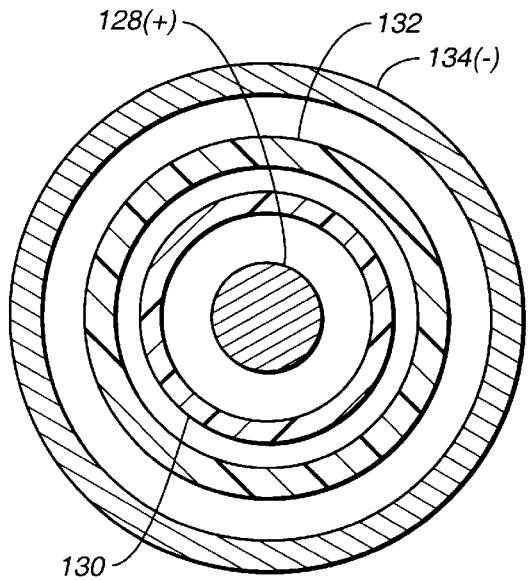
FIG._8

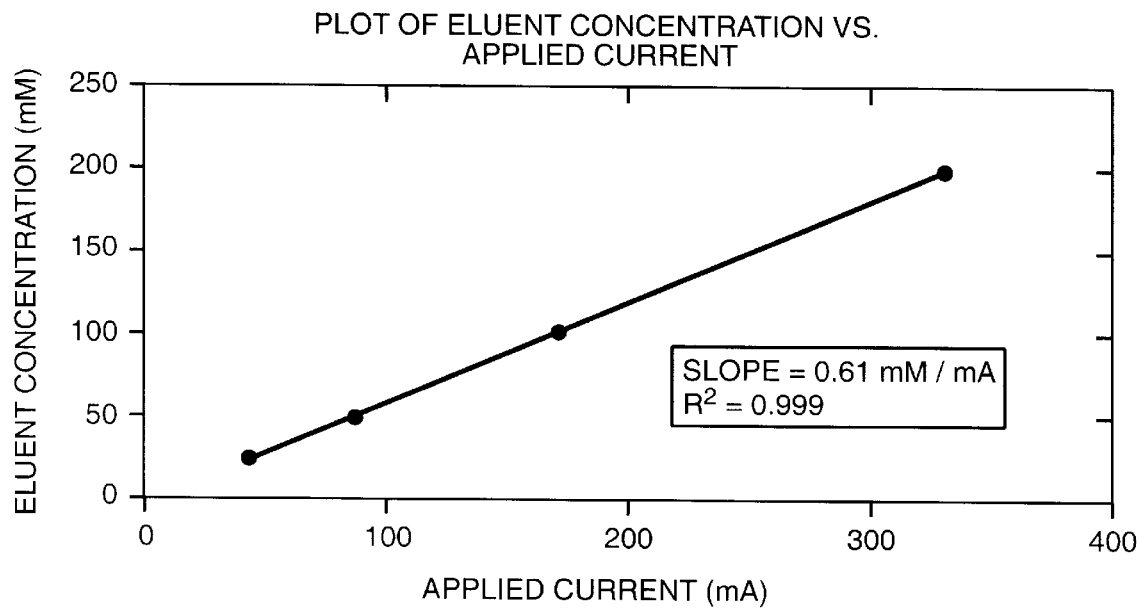
FIG._9
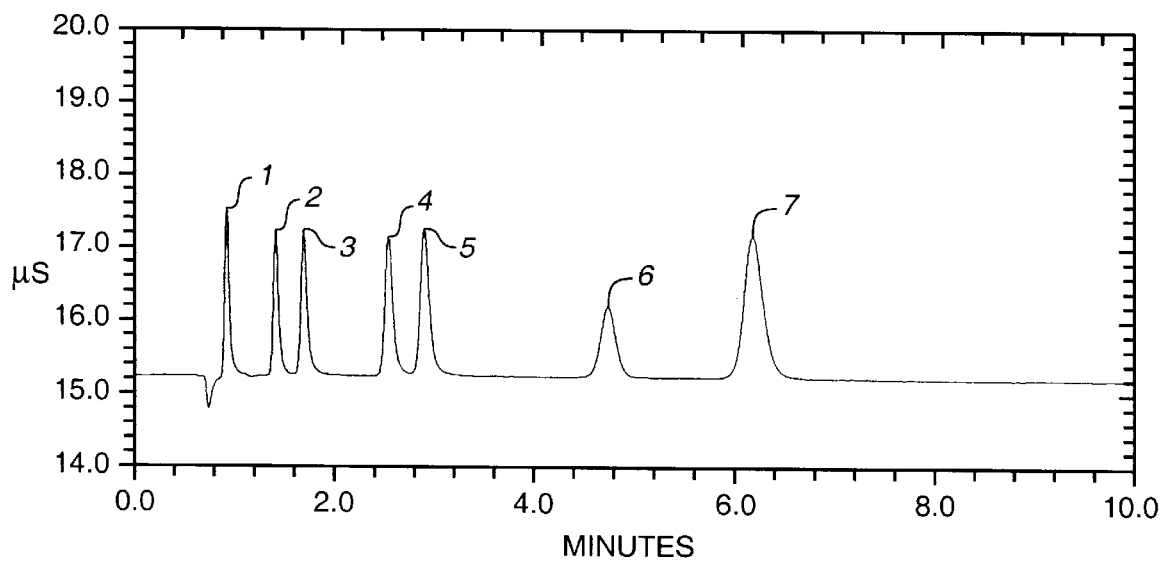
FIG._10

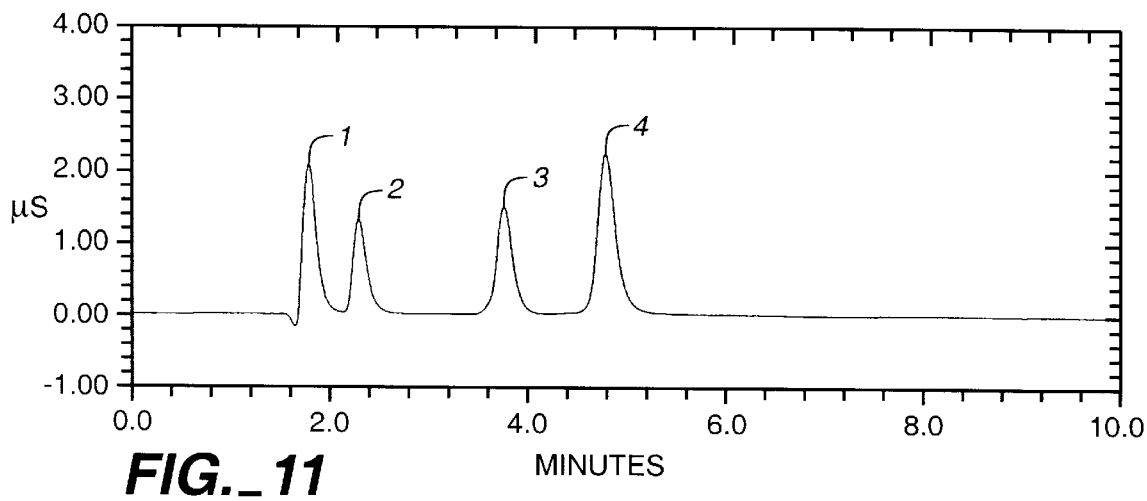
FIG._11
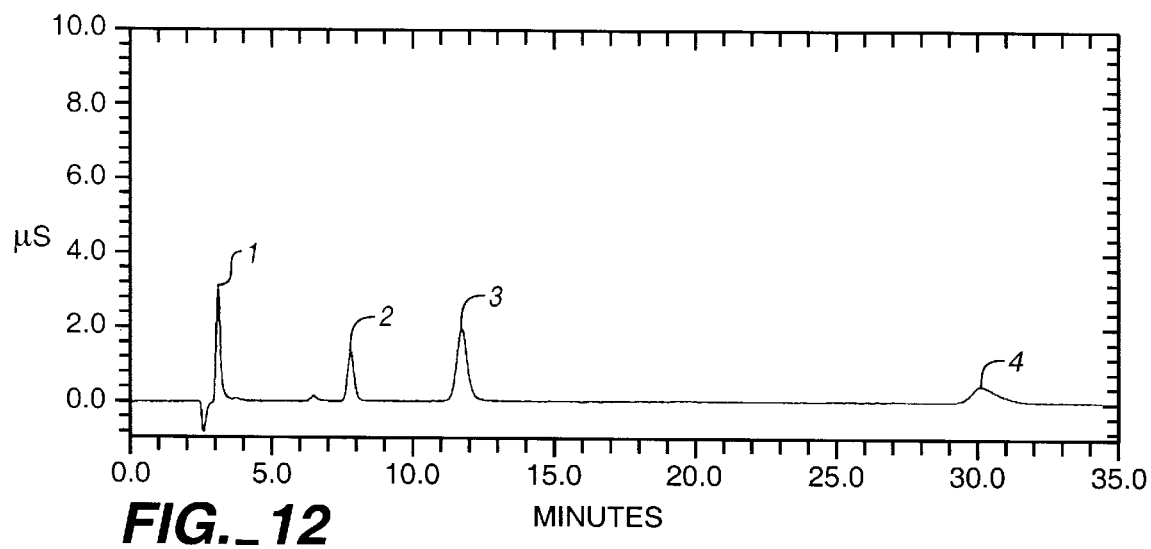
FIG._12
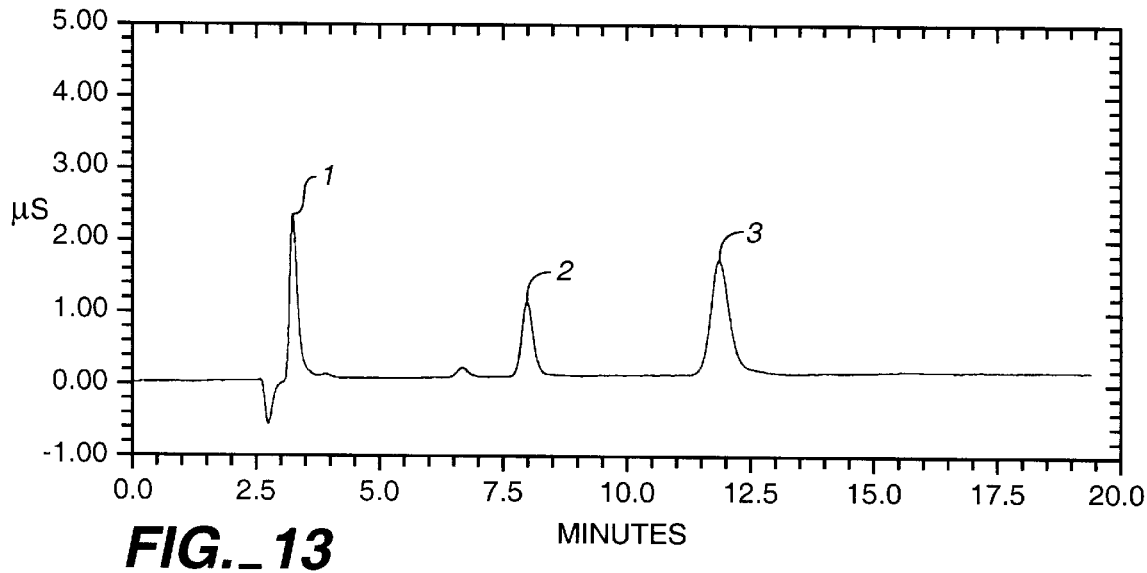
FIG._13

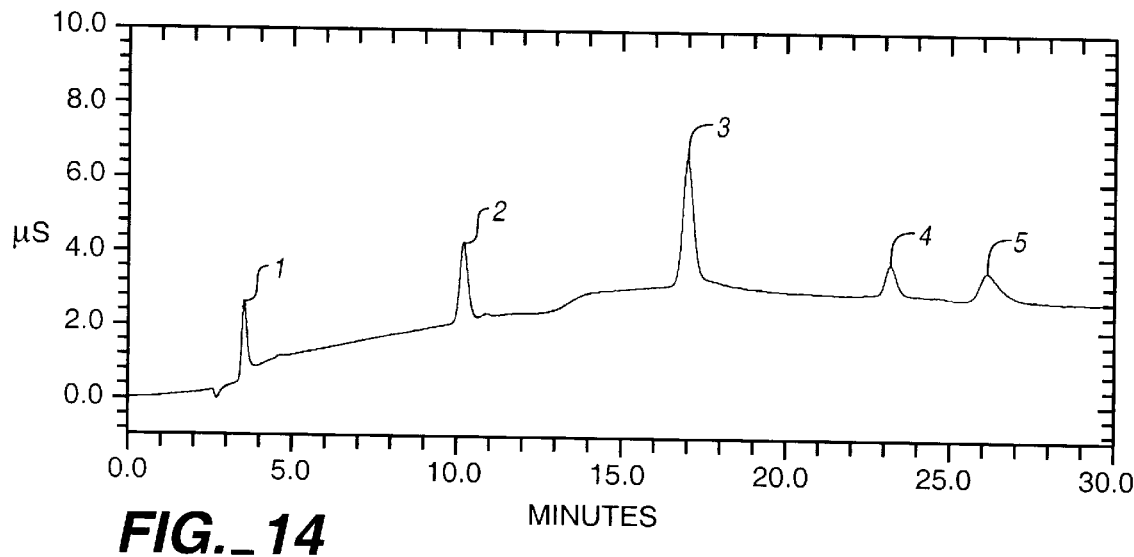
FIG._14
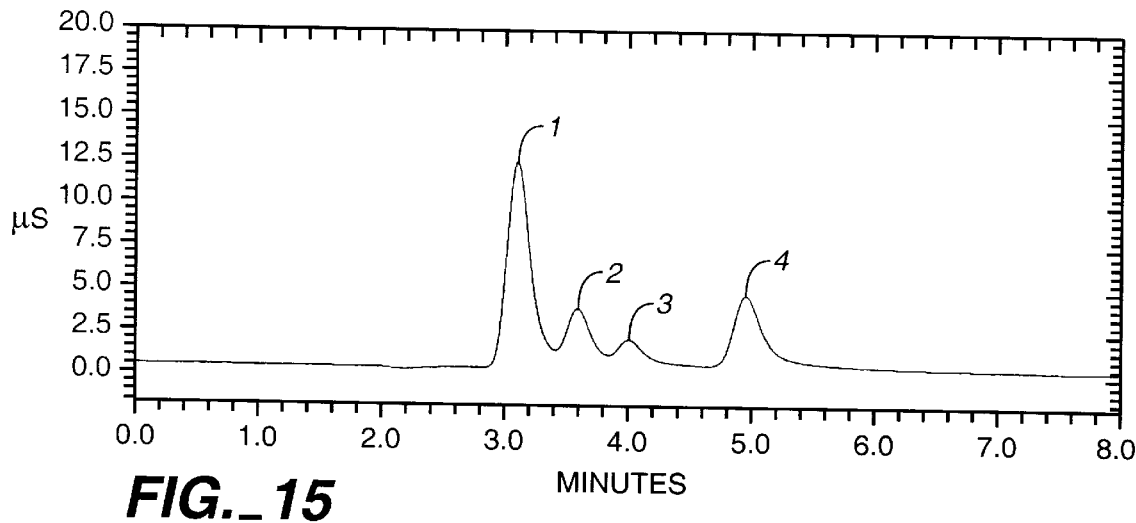
FIG._15
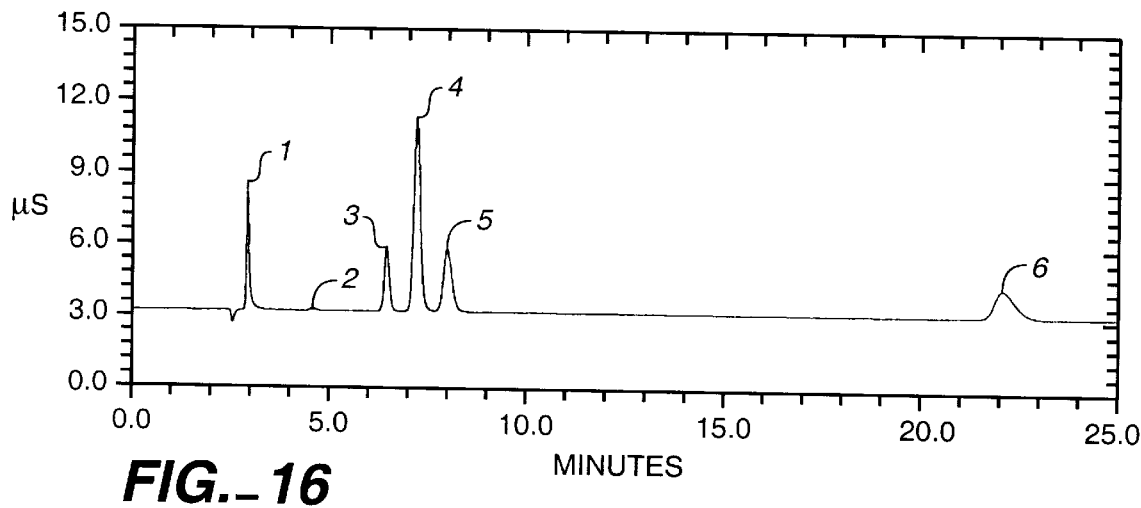
FIG._16

CURRENT-EFFICIENT SUPPRESSORS AND METHOD OF USE

BACKGROUND OF THE INVENTION

The present application relates to a current-efficient device and method for reducing the concentration of matrix ions of opposite charge to ions to be analyzed, and specifically for use of an ion chromatography suppressor or to a pretreatment device.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213; 3,920,397; 3,925,019; and 3,926,559.

Suppression or stripping of the electrolyte is described in the above prior art references by an ion exchange resin bed. A different form of suppressor column is described and published in U.S. Pat. No. 4,474,664, in which a charged ion exchange membrane in the form of a fiber or sheet is used in place of the resin bed. The sample and eluent are passed on one side of the membrane with a flowing regenerant on the other side, the membrane partitioning the regenerant from the effluent of chromatographic separation. The membrane passes ions of the same charge as the exchangeable ions of the membrane to convert the electrolyte of the eluent to weakly ionized form, followed by detection of the ions.

Another membrane suppressor device is disclosed in U.S. Pat. No. 4,751,004. There, a hollow fiber suppressor is packed with polymer beads to reduce band spreading. There is a suggestion that such packing may be used with other membrane forms. Furthermore, there is a suggestion that the function of the fiber suppressor is improved by using ion exchange packing beads. No theory is set forth as to why such particles would function in an improved manner.

Another suppression system is disclosed in U.S. Pat. No. 4,459,357. There, the effluent from a chromatographic column is passed through an open flow channel defined by flat membranes on both sides of the channel. On the opposite sides of both membranes are open channels through which regenerant solution is passed. As with the fiber suppressor, the flat membranes pass ions of the same charge as the exchangeable ions of the membrane. An electric field is passed between electrodes on opposite sides of the effluent channel to increase the mobility of the ion exchange. One problem with this electrodialytic membrane suppressor system is that very high voltages (50–500 volts DC) are required. As the liquid stream becomes deionized, electrical resistance increases, resulting in substantial heat production. Such heat is detrimental to effective detection because it greatly increases noise and decreases sensitivity.

In U.S. Pat. No. 4,403,039, another form of electrodialytic suppressor is disclosed in which the ion exchange membranes are in the form of concentric tubes. One of the electrodes is at the center of the innermost tube. One problem with this form of suppressor is limited exchange capacity. Although the electrical field enhances ion mobility, the device is still dependent on diffusion of ions in the bulk solution to the membrane.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site-to-site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

U.S. Pat. No. 5,045,204 discloses an electrodialytic device using an ion exchange membrane separating two flowing solutions in flow-through channels for generating a high purity chromatography eluent (e.g., NaOH). Water is electrolyzed in a product channel to provide the source of hydroxide ion for sodium which diffuses across the membrane. The patent discloses a mode of eliminating hydrogen gas generated in the product channel.

U.S. Pat. No. 5,248,426 discloses a suppressor of the general type described in U.S. Pat. No. 4,999,098 in an ion chromatography system in which the effluent from the detector is recycled to the flow channel(s) in the suppressor adjacent the sample stream flow channel.

U.S. Pat. No. 5,597,481 disclosed a suppressor-type device of the foregoing type used in sample pretreatment to reduce or suppress matrix ions in the eluent of opposite charge to the analyte ions and then to analyze the analytes in their conductive forms. Using existing suppressor devices, ion exchange interactions and hydrophobic interaction of the analyte, particularly in the eluent flow channel, affects recovery of certain analytes such as oligonucleotides and oligosaccharides. In order to improve recovery, high concentrations of eluents coupled with solvents are generally used. Similarly, in order to elute certain highly charged multifunctional analytes from the chromatographic column, high concentrations of eluents are normally used. High concentrations of eluents, however, are not easily suppressed.

In all of the disclosed approaches, currents higher than theoretically predicted are required for achieving quantitative suppression. Under high eluent concentration conditions, this high current translates into heat generation and high background noise. Therefore, there is a need for a suppressor that would enable suppression of a wide range of eluent concentration and operate near the current-efficient faradaic regime.

There is a need to increase the current efficiency of suppressors and suppressor-like pretreatment devices to permit suppression of a high concentration of eluent without the detrimental effects of excess heat generation. Similarly, in sample preparation applications it would be useful to have a suppressor that would enable good recovery of analytes and suppress high concentrations of eluent or mobile phase.

SUMMARY OF THE INVENTION

In accordance with the present invention, methods and apparatus are provided of improved current efficiency. In one embodiment, an aqueous sample stream including analyte ions of one charge and matrix ions of opposite charge flows through a sample stream flow channel, while flowing an aqueous stream through an ion receiving flow channel separated therefrom by a first ion exchange membrane, and passing a current between the channels to reduce the concentration of the matrix ions. The sample stream flow channel has an upstream sample stream portion containing the matrix ions and an adjacent downstream portion in which the matrix ions have been suppressed. The upstream portion has an electrical resistance no greater than about 0.9 times that of the downstream portion. The ion receiving flow channel includes stationary flow-through first packing of ion exchange material. Neutral or low capacity packing may be disposed in the sample stream flow channel.

In another embodiment, a second ion exchange membrane adjacent to the sample stream flow channel is used defining an ion source flow channel through which another aqueous stream flows. The first membrane has a net charge of no greater than about 0.9 times the net charge of the second membrane. The current is passed between first and second electrodes in electrical communication with the ion source flow channel and ion receiving stream flow channel.

In another embodiment, the downstream portion has a net charge of no greater than about 0.9 times the net charge of the upstream portion.

In a further embodiment, current is passed at a first amperage between the upstream sample stream portion and an adjacent upstream ion receiving stream portion using first and second electrodes, and a second current is passed at a second lower amperage between the downstream sample stream portion and an adjacent downstream ion receiving stream portion using third and fourth electrodes.

In other embodiments, the current is maintained at a substantially constant voltage along the length of the sample stream flow channel. Also, the analyte ions exiting from the sample stream flow channel are detected. For pretreating a sample prior to analysis, the analyte ions exiting from the sample stream flow channel are detected, normally after separating the analyte ions exiting from the sample stream flow channel. For ion chromatography, the analyte ions in the sample stream are chromatographically separated prior to flowing through the ion receiving flow channel. Further, a portion of the sample stream is recycled to the ion receiving stream flow channel and ion source flow channel, if present.

The invention also relates to apparatus for performing the above method.

BRIEF DESCRIPTION OF THE DRAWINGS

FIG. 1 is a schematic view of apparatus for performing chromatography utilizing the recycled detector effluent for the suppressor.

FIG. 2 is an exploded view of a sandwich suppressor device useful in the present invention.

FIG. 3 is a side view of a membrane suppressor illustrating chromatography effluent and detector effluent flow channels in dotted lines.

FIG. 4 is a schematic expanded view of the membranes and screens showing simplified ion transfer in an electrochemical suppressor.

FIGS. 5 and 6 are an exploded view and an assembled cross-section view, respectively, of a suppressor device illustrating a single detector effluent flow channel.

FIGS. 7 and 8 are schematic cross-sectional views of two different tubular forms of electrodialytic suppressors.

FIGS. 9–16 are chromatograms illustrating use of the present invention.

DETAILED DESCRIPTION OF THE PREFERRED EMBODIMENTS

The system of the present invention is useful for determining a large number of ionic analyte so long as the ions are solely anions or solely cations. Suitable samples include surface waters and other liquids such as industrial chemical waste, body fluids, beverages such as fruits, wines and drinking water.

The present invention is directed to a method and apparatus for treating an aqueous sample stream including analyte ions of one charge and matrix ions of opposite charge. In one application, the treatment is in a suppressor for ion chromatography and the matrix ions are the electrolyte ions in the eluent of opposite charge to the analyte ions. In another application, the method and apparatus is used for pretreating an aqueous sample stream prior to analysis, preferably including separation on a chromatography column. In this instance, the matrix ions typically are compounds of high ionic strength in the sample stream (e.g., commercial sodium hydroxide) which can obscure the sample peaks by large interfering peaks of the sample matrix ions. Such matrix ions can severely change chromatography because the sample matrix ion is of such high concentration it becomes the major eluting ion, temporarily overriding the eluent. A typical minimum concentration to warrant pretreatment is when the matrix ion is at least ten times the molar ionic concentration of the chromatographic eluent. Such a system to which the present improvement in current efficiencies is applicable is set forth in Stillian, et al., U.S. Pat. No. 5,597,481, incorporated herein by reference.

As used herein, the term "matrix ion" refers to either the electrolyte in an eluent used for chromatography which is suppressed or whose concentration is reduced to non-interfering levels after separation and prior to detection, or to matrix ions in a sample stream whose concentration is significantly reduced prior to separation and/or detection. Since, in either case, the matrix ions are suppressed in the device, the term "suppressor" will be used generically to include a suppressor for ion chromatography and a pretreatment device including the modifications of the present invention.

For the analysis of anions, the matrix ions typically are a base (e.g., sodium hydroxide or other alkyl metal hydroxides). Other matrix compounds include sodium carbonate, ammonium hydroxide, means over alkyl ammonium hydroxide. For cation analysis, the matrix ions typically are an acid such as a common mineral or organic acid (e.g., sulfuric acid, phosphoric acid or methane sulfonic acid).

The term "packing" refers to stationary flow-through solid material disposed in a flow channel of the suppressor. It can be a screen or a porous monolithic matrix, a resin particle bed or other form. It can be strongly charged, weakly charged or of neutral charge, as will be explained. The term packing is alternatively called "bridging means."

During suppression, the conductivity and noise caused by matrix ions in an analysis stream is reduced. The present invention serves to increase the current efficiency of the suppressors described above. Various embodiments of such current efficient suppressors will be described herein.

In one embodiment, a suppressor of increased current efficiency will be described with respect to a chromatography system of the type using an electrochemical suppressor with detector effluent recycle as described in Stillian, et al., U.S. Pat. No. 5,248,426, incorporated herein by reference.

The specific purpose of the suppressor stage in ion chromatography is to reduce the conductivity and noise of the analysis stream background while enhancing the conductivity of the analytes (i.e., increasing the signal/noise ratio), while maintaining chromatographic efficiency. Thus, the following parameters bear upon the performance of the suppressor: (1) dynamic capacity of suppression, measured as $\mu$Eq./min of eluent for each device; and (2) background conductivity measured as $\mu$S/cm per device.

Referring to FIG. 1, a simplified schematic apparatus for performing the present invention is illustrated using a recycle stream from the detector to the suppressor. The system includes a chromatographic separator, typically in the form of a chromatographic column 10 which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This other system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with column 10 is a suppressor 11 serving to suppress the conductivity of the electrolyte of the eluent from column 10 but not the conductivity of the separated ions. The conductivity of the separated ions is usually enhanced in the suppression process.

The effluent from suppressor 11 is directed to a detector, preferably in the form of flow-through conductivity cell 12, for detecting all the resolved ionic species therefrom. A suitable sample is supplied through sample injection valve 13 which is passed through the apparatus in the solution of eluent from eluent source or reservoir 14 drawn by pump 15, and then passed through the sample injection valve 13. The chromatography effluent solution leaving column 10 is directed to suppressor 11 wherein the electrolyte is converted to a weakly conducting form. The chromatography effluent with separated ionic species is then treated by suppressor 11 and passed through conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

The effluent from conductivity cell 12, referred to herein as the detector effluent, is directed to at least one flow-through detector effluent channel in ion-exchange membrane device 17. The membrane device will be described in detail hereinafter. As illustrated, the detector effluent flows through a splitter valve or tee 19 which separates the detector effluent into two different conduits 20 and 21 to supply the detector effluent to flow-through channels on opposite sides of the two membranes of the suppressor adjacent the central sample stream flow channel and then to waste through conduit 22. In one alternative, the detector effluent flows through such channels sequentially and then to waste. The chromatography effluent flows from chromatographic column 10 to membrane device 17 through conduit 23, and from the membrane device to the conductivity detector through conduit 24.

Sandwich Suppressor Device

Referring to FIGS. 2–5, a device is illustrated in the form of a sandwich suppressor device including a central sample stream flow channel defined on both sides by ion-exchange membranes to the exterior of which are an ion receiving flow channel and an ion source flow channel, respectively.

Referring specifically to FIGS. 2, 3 and 4, membrane device 17 is illustrated which includes a central sample stream flow channel 31 flanked by such ion receiving and ion source flow channels. Membrane device 17 includes means defining a sample stream flow channel in the form of a sample stream compartment, partially bounded by sample stream gasket 30 defining a central cavity. To minimize dead space in the cavity, it is preferable to form both ends of the flow channels in a peak or V-shape. Stationary flow-through packing, preferably bridging means in the form of sample stream screen 32, may be disposed in the cavity. Ion exchange membrane sheets 34 and 36 are mounted to extend along opposite sides of screen 32 and, together with gasket 30, define the outer perimeter of the sample stream flow channel. Openings 36a and 36b are provided for sample stream inlet and outlets to the sample stream flow channel.

Gaskets 38 and 40 are mounted to the facing surfaces of ion exchange membrane sheets 34 and 36, respectively, and define an ion receiving flow channel 35 and an ion source flow channel 37, respectively. In one embodiment, packing or bridging means are provided in ion exchange flow channels 35 and 37, in the form of ion exchange screens 41 and 43, respectively. Openings 40a and 40b are provided for inlet and outlet detector effluent flow-through gasket 40. To simplify connections with the external flow lines, it is preferable to form the chromatography effluent flow channel slightly longer than the flanking regenerant flow channels.

As illustrated, spaced electrode means in the form of flat plate electrodes 42 and 44, are placed on the exterior sides of gaskets 38 and 40, respectively, extending substantially across the length and width of the chambers in the gaskets. An electrical potential is applied across the electrode means. Electrode 42 includes openings 42a and 42b to permit the inlet and outlet flow of detector effluent solution to ion receiving flow channel 35 Similarly, electrode 44 includes inlet and outlet openings 44a and 44b, respectively, for detector effluent liquid flow and ion source flow channel 37 and gasket 40, and also defining inlet and outlet openings 44c and 44d for the chromatography effluent flow channel defined by gasket 30.

External support blocks 46 and 48 are formed of a rigid nonconductive material, such as polymethylmethacrylate, or polyether-ether ketone (PEEK) and serve to provide structural support for the remainder of membrane device 17. Referring to FIG. 3, fittings 50 and 52 are provided for detector effluent inlet and outlet lines 54 and 56, respectively. Similarly, fittings 58 and 60 are provided for detector effluent inlet and outlet lines 62 and 64, respectively. Fittings 66 and 68 are provided for chromatography effluent inlet and outlet lines 70 and 69, respectively. The fittings may be mounted to the support blocks by any conventional means such as mating screw threads.

The above assembled sheets and gaskets are mounted under pressure supplied by bolts 71 to form liquid-tight seals. Also, by use of such pressure in combination with appropriate sizing of the screen (or other bridging means described below) in comparison to the flow channel dimensions, the screen extends substantially the entire distance across the flow channels and contacts the membranes, resulting in significantly improved ion transport and efficiency. It is preferable for maximum membrane transfer efficiency to connect the lines to the chromatography effluent and detector effluent flow channels for countercurrent flow.

Ion-exchange membrane sheets 34 and 36 may be of a type such as disclosed in U.S. Pat. No. 4,486,312. In particular, such sheets may be cation-exchange or anion-exchange membranes with polyethylene, polypropylene, polyethylene-vinylacetate-based substrates. Other suitable substrates include poly-vinylchloride or polyfluorocarbon-based materials. The substrate polymer is solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alkylvinylpyridines. As an example, to form a cation-exchange membrane, the sheets grated with styrene monomers are functionalized suitably with chlorosulfonic acid, sulfuric acid, or other $SO_2$ or $SO_3$ sources. To form an anion-exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 10 mil thick, and preferably no more than 2–4 mil when wet. Suitable polyethylene substrate membranes of the foregoing type are provided by RAI Research Corp., Hauppauge, N.Y. (the cation exchange membrane provided under designation R5010 (0.008 inch thick) and the anion-exchange membrane under designation R4015 (0.004 inch thick)). Other cation exchange membranes supplied by the same company which are fluorocarbon based include R1010 (0.002 inch thick) and R4010 (0.004 inch thick).

Sample stream screen 32 may be formed integral with chromatography effluent gasket 30 or may be inserted independently into the effluent flow channel. A screen integral with the surrounding gasket material may be formed by cutting a gasket from plastic sheet to include the desired flow path and pressing this gasket into a rectangular piece of screen such that only the flow path is not covered by the gasketing material.

Ion exchange packing in the form of screens 41 and 43 may be constructed in the same manner as set forth with respect to screen 32.

For a flat sheet suppressor, the packing preferably includes continuous portions which extend substantially the entire distance across flow channels 31, 35 and 37 transverse to flow. In the embodiment of FIGS. 2 and 3, this distance extends between membrane sheets 34 and 36 and between the same membrane sheets and electrodes 42–44, respectively. In an alternate embodiment of FIG. 6 described below, only one membrane is used which separates ion receiving flow channel 35 from sample stream flow channel 31. The packing defines a continuous convoluted flow-through passageway in the flow channel in which it is disposed along substantially the entire length of the membrane. This creates turbulence and thus increases the efficiency of mixing and transfer of the ions across the membrane as described below. The physical configuration of the screen may vary so long as its bridging function and turbulence-producing function is accomplished. Thus, the screen may vary so long as its bridging function and turbulence-producing function is accomplished. Thus, the screen may be provided with a weaving pattern either perpendicular or diagonal to the direction of flow. Also, the fibers may be smooth or contain protrusions such as bumps.

A major function of the flow-through packing 41 and 43 in ion exchange form is to provide a site-to-site path for ions in the direction transverse to the flow channel to increase the efficiency of ionic transfer across the ion-exchange membrane as more fully described below. Such packing in the form of a screen may be functionalized for this purpose in a manner analogous to the functionalization of the ion-exchange membranes set forth above. Suitable screens may be formed of the same base polymers grafted with the same functionalizing monomers as those set out above for the membranes.

Good chromatographic efficiency of the screen embodiment of the flow-through ion-exchange packing may be achieved using a relatively small mesh (measured after functionalization), e.g., on the order of 110 $\mu$ mesh size or less with relatively thin fibers, e.g., on the order of 0.004 inch in diameter. An open area in flow channels 35 and 37 on the order of 5% to 70% (preferably, on the order of 8%) provides excellent efficiencies. A suitable proportion of grafting monomer to grafting polymer substrate is on the order of 5%–50% (preferably about 25% to 35%). In order to obtain maximum efficiency, flow channels 35 and 37 should be fairly narrow, e.g., on the order of 0.5 cm, with the weave pattern oriented diagonally to the direction of flow. As the exposed membrane surface area increases, suppression capacity increases. However, practical limits are prescribed by known principles of chromatography. For example, to minimize band broadening, a minimum volume is desired. To maximize the dynamic capacity, screens 41–43 may be functionalized to relatively high ion exchange capacity, e.g., 2 meg/g.

In the embodiments of FIGS. 2 and 3, an electrical potential from a direct current source (not shown) is applied between electrodes 42 and 44 from any suitable source. The electrodes are formed of highly conductive material which is inert to the solutions being passed through the membrane suppressor. Platinum is a preferred form of electrode for this purpose.

In one mode of operation of the suppressor device 17, effluent from chromatographic column 10 is directed through sample stream flow channel 31 bounded on both sides by ion-exchange membranes 34 and 36 partitioning the detector effluent from the chromatography effluent. The detector effluent flows from the conductivity cell through channels 35 and 37. The membrane is preferentially permeable to ions of the same charge as the exchangeable ions of the membrane and resists permeation of ions of opposite charge. The exchangeable ions of the membrane are in the ion form necessary to convert the developing reagent of the eluent to a weakly ionized form. For maximum capacity, the detector effluent flow is countercurrent to the sample stream flow. The chromatography effluent from chromatographic column 10 is passed through the sample stream flow channel and contacts both membranes. The membranes are simultaneously contacted on their outer sides with the detector effluent flowing in the opposite direction through the detector effluent flow channel so that membrane forms a selective permeability partition between the detector effluent and the sample stream from the chromatography column. Ions extracted from the same stream at the active ion-exchange sites of the membranes are diffused through the membranes and are exchanged with ions of the detector effluent, and thus diffused ultimately into the detector effluent. Application of a potential across the electrodes increases the mobility of the ions across the membrane. The resolved ionic species in the effluent leaving the suppressor device are detected, as with a conductivity detector.

FIG. 4 schematically illustrates the electrochemical operation of the present invention for a particular system, using a sandwich suppressor with screens 32, 41 and 43 in flow channels 31, 35 and 37, respectively, and applying an electrical potential between spaced electrodes. The system illustrated is for anion analysis and includes sodium hydroxide as the electrolyte of the effluent to be converted into weakly ionized form ($H_2O$) in the suppressor. Thereafter, the solution passes through the conductivity cell and is recycled to flow channels 35 and 37. The ion-exchange membrane sheets allow the positively charged sodium and hydronium ions to permeate across the membrane together.

A suitable ion-exchange membrane for this purpose is a sulphonated polyethylene sheet. Hydroxide ions tend not to permeate the membrane sheet because of Donnan Exclusion forces. Thus, the sodium hydroxide stream is converted to deionized water in the chromatography effluent flow channel and the sodium ions permeate the membrane sheet and are dispersed in the negatively-charged detector effluent flow channel as NaOH and thus ultimately routed to waste through the detector effluent outlet lines. Applying a potential across electrodes 42 and 44 increases the kinetics of ion flow across the membrane and thereby increases capacity and, thus, the suppression efficiency of the suppressor device.

In the illustrated embodiment, the positively charged sodium ions of the electrolyte in channel 31 electromigrate under the influence of the electric field, across the negatively charged membrane 34 into the detector effluent channel. The hydronium ions generated at the anode by electrolysis of water, flow from the positively-charged flow channel 37 across membrane 36 into flow channel 31 to form water with hydroxide ions therein. The sodium ions, being attracted to the negative electrode, are more rapidly removed leading to a substantial increase in the capacity of the suppressor device.

In operation of the system of FIG. 4, in flow channel 37, hydronium ion is generated at the anode according to the following equation and passes through membrane 36

$$H_2O - 2e^- \rightarrow 2H^+ + \tfrac{1}{2}O_2 \qquad (1)$$

In flow channel 31, the sodium ion passes through membrane 34 under the influence of the electric field. Hydroxide is converted to water according to the following equation:

$$OH^- + H^+ \rightarrow H_2O \qquad (2)$$

In flow channel 35, the sodium ion is converted to NaOH with hydroxide ion produced at the cathode by the following equation:

$$2H_2O + 2e^- \rightarrow 2OH^- + H_2 \qquad (3)$$

High capacity ion exchange screens 41 and 43 substantially increase the capacity of the suppressor device to remove ions from the chromatography effluent sample stream. The threads of the screen preferably extend substantially across the flow channels transverse to flow to contact both membranes.

The functionalized screens 41 and 43 include exchangeable ions of the same charge as those of the membranes. In this manner, the screen provides a direct site-to-site contact between the membrane walls for the ions to be diffused through the membranes. It has been found that the capacity of the system is significantly increased by the use of such functionalized screens.

Referring again to FIG. 4, sample stream flow channel 31 may include weakly charged packing such as lightly sulfonated packing (screens) of low capacity. In a preferred embodiment the capacity of such packing would be less than 0.1 meq/g. In a more preferred embodiment the capacity of such packing would be less than 0.01 meq/g. The sample stream flow channel 31 in an alternative embodiment may include neutral packing material (screen) of substantially no ion exchange capacity.

The reduction in the ion exchange capacity for the packing (screens) is achieved by reducing the extent of functionalization; for example, optimizing the sulfonation conditions for a cation exchange material by time or temperature or both. Optimizing the graft level is another means for reducing the capacity of the packing material.

The potential to be applied to the electrodes in the above system may be relatively low due to the presence of the functionalized screens 41 and 43. Thus, capacity is substantially improved with a voltage of about 1.5–20 VDC, preferably about 2–8 VDC.

While the above sandwich suppressor embodiment includes a center sample stream flow channel 31 separated by two membranes from two coextensive flow channels 35 and 37, the system is also applicable to the use of a single ion receiving stream flow channel separated from the sample stream flow channel by a single membrane.

Referring to FIGS. 5 and 6, another embodiment of suppressor 70 is illustrated using a single membrane. Suppressor 70 includes upper rigid support block 72 with sample stream flow channel wall 73 and lower support block 74 with ion receiving flow channel wall 75, separated by an ion-exchange membrane 76 of the type described above.

The chromatography effluent flows into the suppressor device through effluent inlet 78, fitting 80 and flows along a sample stream flow channel defined by wall 73, through screen 94 and then through fitting 82 and out sample stream outlet line 84. Similarly, detector effluent solution flows from inlet line 86 through fitting 88 across the ion receiving flow channel defined by wall 75, out fitting 90 and through ion receiving flow channel outlet 92 to waste. The device of FIGS. 5 and 6 is used in the overall system of FIG. 1 in place of the device of FIGS. 2–5.

The liquid flows through the channels formed by the spacing among the projections. The dimensions of the projections and spacing is selected to provide the desired frequency of contacts with the flowing ions to increase their mobility across the membrane and to create sufficient turbulence for increased mixing efficiency.

Suitable eluent solutions for ion chromatography of anions include alkali hydroxides, such as sodium hydroxide, alkali carbonates and bicarbonates, such as sodium carbonate, alkali borates, such as sodium borate, combinations of the above, and the eluent systems of the aforementioned patents.

The system of the present invention is also applicable to the analysis of cations (e.g., lithium, sodium, ammonium, potassium, magnesium, and calcium). In this instance, the electrolyte of the eluent is typically an acid which does not damage the membrane. Methane sulfonic acid has been found to be inert to the membrane under electrolytic conditions. Other acids such as nitric acid and hydrochloric acid produce electrochemical by-products that may damage the membrane and are, thus, not generally preferred for that typical membrane.

In cation analysis, the flow of the electrolyte ion is from the cathode toward the anode, rather than the reverse as in anion analysis and the ion exchange screens and membranes are aminated and permeable to anions. Thus, in the negatively charged ion source flow channel, water is converted to hydroxide ion and hydrogen gas. The hydroxide ion passes through the adjacent membrane into the sample stream flow channel and combines with hydrogen ion (or an amine or other basic organic molecule group) to form weakly ionized electrolyte. The negatively-charged transmembrane ion travels through the second membrane into the positively-charged ion receiving flow channel under influence of the anode to form an acid which passes to waste. In summary, for cation analysis, the electrical charges of the analyte, eluent reagent, and membranes are reversed for cation analysis and anion analysis.

In a single membrane suppressor, gases are generated in the chromatography effluent which can interfere with detection in the conductivity cell. For example, for ion analysis, oxygen is generated in the detector effluent flow channel. One way to remove the oxygen is to pass the effluent from the sample stream flow channel through a gas diffusion removal device, using a gas diffusion membrane, prior to reaching the conductivity cell. One such device is disclosed in U.S. Pat. No. 5,045,204. In another embodiment, a gas diffusion membrane forms a wall defining the opposite side of the chromatography effluent flow channel from the ion exchange membrane. An inert gas stream such as nitrogen, may be flowed in a channel bounded on one side by the gas diffusion membrane, preferably countercurrent to the chromatography effluent flow. In this manner, the solution leaving the chromatography effluent flow channel is degassed prior to reaching the conductivity cell. In either event, a suitable gas diffusion membrane is a gas diffusion membrane such as one sold under the trademark Accural® or Celgard®.

The above system illustrates an ion exchange screen as the preferred flow-through ion exchange packing. However, it should be understood that other ion exchange packing may also be employed for the sandwich suppressor or other relatively flat suppressor. For example, ion exchange particles may be packed in the flow channels for this purpose. Here, it would be preferable to include some mode to keep the ion exchange particles in the device by using a porous polymeric support that has smaller pores than the resin being used, such as sintered polyethylene available from General Polymeric.

Referring to FIG. 7, a schematic cross-sectional view of a tubular form of the electrodialytic suppressor of the present invention is illustrated. In this instance, it is assumed that the sample stream channel is the lumen of the innermost tube. The device includes anode 122 (in the form of a rod or wire, e.g., formed of platinum, gold, carbon or stainless steel), cation exchange membrane 124, and outer wall 126, which may be formed of a conductive material to serve as the cathode. In one embodiment, high capacity flow-through ion exchange packing in the form of a bed of ion exchange resin particles is disposed in the ion receiving flow channel with low capacity or neutral resin or open space in the sample stream channel. This system is comparable in general function to the one illustrated in FIG. 4. Alternatively, the ion receiving flow channel may be the lumen of the inner tube. In this instance, the polarities of the electrodes are reversed. Membrane 124 may be formed of stretched or unstretched tubular ion exchange membranes, e.g., Nafion 811X from Perma-Pure Products, J.S. Outer wall 126 may be formed of an 18 gauge stainless steel (SS) tubular case.

FIG. 8 illustrates a tubular type of dual-membrane suppressor of similar function to the sandwich membrane suppressor. It is generally constructed by inserting a length of suitably inert wire inner electrode 128 into a length of tubular inner membrane 130 which is itself inserted inside a length of somewhat larger diameter tubular outer membrane 132 and enclosing the whole assembly in stainless steel tube 134 of appropriate dimensions. The outer tube itself functions as the electrode, connections being made at the ends to allow access to the flow channels between the inner electrode and inner membrane, between the two membranes (annulus) and between the outer membrane and stainless steel case. High capacity flow through ion exchange packing in the form of a bed of ion exchange resin particles is disposed in the ion receiving flow channel with neutral or low capacity or open space in the sample stream channel.

The power requirements for this system are dependent to some extent upon the flow rate through the system and the concentration of electrolyte solution. For this purpose, a suitable flow rate or chromatography effluent is about 0.01 to 10 mls/min. and, preferably, 0.25 to 2 mls/min. The concentration of eluent varies between about 5 and 500 mM. Suitable power supply requirements are about 2 to 12 V at 0.001 to 2 A. Suitable power requirements are 2 to 12 volts at 0.001 to 2 A. This applies to both the flat membrane suppressor and tubular membrane assembly.

Other alternative configurations (not shown) of the suppressor can be used in accordance with the present invention. For example, referring to the suppressor of FIGS. 2–4, the positions of screens 41 and 43 may be reversed with the positions of electrodes 42 and 44, respectively. Specifically, in such alternative configurations, electrodes 42 and 44 extend along, and are pressed flush against, ion exchange membranes 34 and 36, respectively. The electrodes are in contact with the solution flowing through the outside flow channels 35 and 37. In this instance, the electrodes include openings to permit ion transport across the ion exchange membranes between the outside flow channels 35 and 37 and the sample stream flow channel. Such openings may be formed in a number of known ways, e.g., by punching of spaced holes (typically from 0.010" to 0.250" across), or by forming the electrodes of a woven screen, or by notching an inert foil electrode so that the electrode forms a zig-zag or serpentine pattern along the length of the chamber. For example, platinum wire bent into a zig-zag pattern can be used, however, platinum or platinum plated foil is preferable to prevent excessive resistive heating.

In yet another embodiment (not shown), a "hybrid" suppressor may be formed in which the electrode and screen is in the configuration illustrated in FIGS. 2–4 for one of the outside flow channels while in the opposite outside flow channel the electrode and screen are reversed in the manner described in the previous paragraph. An effective hybrid configuration for an ion analysis is formed in which an anode with spaced openings is flush against the ion exchange membrane and the cathode (the compartment to the left of FIG. 3) is in the configuration illustrated in FIGS. 2–4. The same configuration is preferred for cation analysis.

According to the present invention, suppressor current efficiency is increased. In such devices, the upstream portion of the device includes a concentration of the matrix ions which decreases in the downstream portion of the channel to a level where the matrix ion is "suppressed", i.e., present at a level which does not significantly interfere with subsequent analysis. Thus, it is preferable to provide a maximum current in the upstream portion in which suppression of the matrix ion takes place. In the downstream portion in which suppression is substantially complete, the current does not provide sufficient beneficial effect to counter-balance its negative effects such as generation of high background noise and heat caused by the application of the electrical field. Thus, one of the objectives of the present invention is to provide a lower electrical resistance in the upstream portion in which the matrix ions are present and being suppressed in comparison to the downstream portion.

It is preferable that the upstream portion of the sample stream flow channel in which matrix ion is present and suppression occurs have an electrical resistance no greater than about 0.9 times that of the downstream portion in which suppression is substantially complete. Suppression is considered substantially complete at a distance along the sample stream flow channel when the matrix ion concentration has been reduced by at least 95% from the concentration at the beginning of the flow channel. This typically occurs at a distance of about 20 to 80% (more typically about 40 to 60%) along the length of the sample stream flow channel. Preferably, the electrical resistance ratio of the upstream and downstream portions is no greater than about 0.7 to 0.9, and most preferably no greater than about 0.7.

The resistance of the upstream and downstream portions is determined as follows. A suppressor of the type sold by Dionex Corporation under the ASRS name is fitted with two anodes and two cathodes such that the electrodes flank the upstream and downstream portions of the ion source and receiving channels, respectively. When powered and monitored for suppression with 100 mM of NaOH at a flow rate of 1 mL/min, this unit provides average upstream and downstream portion resistances. For example, using 100 mA settings for the two zones the measured resistances were approximately 40.2 and 35.3 ohms, respectively, suggesting that the upstream portion was more resistive than the downstream portion. In contrast, the devices of the present invention have the upstream portion less resistive than the downstream portion. For example, in the above example when the current to the upstream portion was 100 mA and the downstream portion was 75 mA, the device resistances were approximately 40.2 and 45.46 for the upstream and the downstream portions, respectively. The current efficiency went up from 80% to 92% in the above example.

An alternative means for demarking the upstream and downstream zones is by disassembling the suppressor unit and visually examining the upstream and downstream zones in the eluent channel. The ion exchange material in the eluent form shows a lighter coloration in comparison to the downstream portion, which is in the suppressed form. For example, an ASRS suppressor of the prior art with 100 mM NaOH at 1 mL/min and run at 500 mA and 4 V shows 50% of the eluent channel in the eluent form. Similarly, a CSRS suppressor of the prior art run with 22 mN $H_2SO_4$ at 100 mA and approximately 3.6 V shows the eluent zone to be 50% of the eluent channel. The suppressed form is less resistive than the eluent form, hence in both of the above devices the upstream portion is more resistive than the downstream portion, hence the devices are not current efficient.

In the above system, one way to increase current efficiency is leave the sample stream flow channel open without packing or to use packing which is of neutral charge or of low capacity relative to the packing of high capacity ion exchange material in the ion receiving flow channel and, for a two membrane suppressor, in the ion source channel. While the above description refers to the stationary flow-through packing of ion exchange material in the form of a high capacity charged screen, other forms of packing may also be employed as described above. Such other packing forms of ion exchange material include packed beds of ion exchange resin or monolithic materials of charged material with sufficient porosity for the flow of an aqueous liquid stream through them. The packing in the ion receiving channel has a substantially higher capacity than ion exchange packing in the sample flow channel, if present. Thus, if a charged packing is used in the sample stream flow channel, it preferably is of low capacity, with a capacity of substantially less than that of the packing in the ion receiving flow channel. Suitably, the ratio of total capacities of the packing in the sample stream flow channel to that in the ion receiving stream flow channel is no greater than about 0.9, and preferably no greater than about 0.7 to 0.5, and more preferably no greater than about 0.1.

A suitable low capacity packing in the sample stream flow channel has a capacity less than about 0.1 meq/g and preferably less than about 0.01 meq/g. This difference in the capacity of the sample stream flow channel and the ion receiving flow channel and ion source flow channel (if present) will be referred to herein as the "packing principle." This principle can be used in combination with all of the other embodiments of current efficiency described hereinafter.

The current efficiency by this approach is substantially increased in comparison to having fully charged packing in the sample stream flow channel as described in the prior art, e.g., in U.S. Pat. No. 5,248,426. The mechanism of suppression in the cited prior art is described as follows. The electrochemically-generated hydronium ions at the anode are transported across the ion exchange bridging means towards the cathode and migrate into the eluent channel. For each H+ ion transported into the eluent channel, either a Na+ ion or a H+ ion is transported across the channel towards the cathode and forms either sodium hydroxide or water at the cathode. The current used in forming water is the excess current and is not used for suppression. Since the ion exchange means in the hydronium form is less resistive than the sodium form, transport of hydronium, particularly across the eluent channel, is preferred and hence the device is not current efficient. In these devices transport of hydronium into the channel does not guarantee transport of sodium out of the eluent channel. Thus, the presence of functionalized screen drives up the current requirement for suppression and an excess of hydronium ions is required to ensure complete suppression of the eluent.

By reducing the capacity of the eluent screen, the present invention forces the current to be carried by the eluent alone in the eluent channel. Thus transport of hydronium into the eluent channel guarantees transport of sodium out of the eluent channel, and formation of water by transport of hydronium across the eluent channel and to the cathode is minimized. Thus suppression is guaranteed with near faradaic efficiency.

The reduction in capacity for screens is achieved by using either a neutral unfunctionalized screen or by reducing the extent of functionalization; for example, optimizing the sulfonation conditions for a cation exchange material by time or temperature or both. Optimizing the graft level is another means for reducing the capacity of the packing material.

The current required to suppress a given concentration of eluent with 100% faradaic efficiency can be calculated from $$I=FCV/60$$

wherein

I is current mA
F is Faraday's constant (coulombs/equiv.)
C is the concentration of eluent in M
V is the flow rate in mL/min.

Now, the current required to suppress 20 mM of NaOH eluent with 100% faradaic efficiency can be calculated as approximately 32 mA.

In FIG. 1, when a neutral screen or no screen is used in the eluent channel, then 100% of the current is carried by the eluent and the device is expected to show 100% faradaic current efficiency. One way to compare current efficiency to capacity is to test the suppressor using an aqueous stream of 100 mM NaOH at 1 mL/min. Current efficiency was determined by optimizing the current required for suppression (with a variance of ±10 mA). The results are set forth in the following table.

TABLE 1

| Eluent screen capacity | Estimated Current Efficiency (%) | Volts |
| --- | --- | --- |
| 0.925 meq/g (prior art suppressor) | 67 | 3.71 |
| 0.005 meq/g (device of present invention) | 92 | 5.2 |
| Neutral screen - 0 meq/g (device of present invention) | 95 | 5.0 |

In the case where the neutral screen is replaced by a low capacity, lightly functionalized screen bulk of the current is still transported by the eluent with a small percentage of the current being wasted in formation of water due to transport of excess $H^+$ across the screen. The voltage applied across the above disclosed suppressor devices is comparable to the voltage generated in an SRS device (4–9 V) as disclosed in U.S. Pat. No. 5,246,426.

In the sandwich suppressor described above, high capacity ion exchange packing of the type described regarding the packing in the ion receiving flow channel also is used in the ion source flow channel. This is a preferable form of the sandwich suppressor because the high capacity packing allows efficient transport of the electrochemically generated hydronium from the anode (in the case of anion analysis) to the membrane interface. Similarly, fast transport of sodium from the eluent channel to the cathode becomes possible in the presence of high capacity ion exchange packing. The presence of packing in the channels keeps the voltage drop across the entire device within acceptable limits. In the absence of ion exchange packing, it is not possible to use the suppressed effluent (e.g. water) as the regenerant (as used in the recycle mode). Additionally, the device voltage becomes very high.

Referring to FIGS. 5 and 6, another embodiment of suppressor 70 is illustrated using a single regenerant flow channel. Suppressor 70 includes upper rigid support block 72 with sample stream flow channel wall 73 and lower support block 74 with ion receiving flow channel wall 75, separated by an ion-exchange membrane 76 of the type described above.

The chromatography effluent flows into the suppressor device through effluent inlet 78, fitting 80 and flows along the sample stream flow channel defined by wall 73, through screen 94 and then through fitting 82 and out chromatography effluent outlet line 84. Similarly, detector effluent solution flows from inlet line 86 through fitting 88 across the ion receiving flow channel defined by wall 75, out fitting 90 and through detector effluent outlet 92 to waste. The device of FIGS. 5 and 6 is used in the overall system of FIG. 1 in place of the device of FIGS. 2–4.

The liquid flows through the channels formed by the spacing among the projections. The dimensions of the projections and spacing is selected to provide the desired frequency of contacts with the flowing ions to increase their mobility across the membrane and to create sufficient turbulence for increased mixing efficiency.

As illustrated, the detector effluent is recycled to the ion receiving flow channel, and if present, to the ion source flow channel. While this is efficient for the reasons set forth above, it should be understood that this system is applicable to suppression without such detector recycle as illustrated in U.S. Pat. No. 4,999,098, incorporated herein by reference.

As set out above, electrochemical suppressor device of the type described above can be used in a pretreatment device prior to analysis of the analyte. One pretreatment device and system is illustrated in U.S. Pat. No. 5,597,481, incorporated herein by reference. This pretreatment device is substantially the same as the foregoing suppressor. The matrix ion which is removed in the pretreatment device is of opposite charge to the analyte ion. The improvements in current efficiency described herein are also applicable to the pretreatment device as set forth in the patent.

Another embodiment of increasing current efficiency according to the invention is applicable to two membrane suppressors. Here, the net charge of one of the membranes is greater than the charge of the other one. In one embodiment, the membrane separating the ion source channel from the sample stream flow channel has a net charge no greater than about 0.9 times the net charge of the membrane separating the sample stream flow channel from the ion receiving channel. Preferably, this ratio is no greater than 0.7 times, and more preferably no greater than 0.5 times.

A preferred means for altering the net charge of the two membranes is by using two different functionalities, a strongly ionized functionality in combination with a weakly ionized functionality. One sandwich suppressor of the general type illustrated in FIG. 4 suitable for anion analysis includes a strong cation exchange membrane 36 (sulfonated membrane) forming the eluent channel in the anodic side and a weak cation exchange membrane 34 (carboxylated membrane) forming the eluent channel in the cathodic side. This combination of functionality is a convenient means of accomplishing different net charges on the two membrane surfaces.

Hydronium that is generated at the anode is efficiently transported across the strong cation exchange membrane and into the eluent channel by high capacity ion exchange packing in the ion source flow channel. The weak cation exchange membrane readily allows transport of eluent cations (such as sodium ions in the case of sodium hydroxide eluent) across the membrane towards the cathode, while retarding the transport of hydronium ions. The weak cation exchange membrane is less resistive in the sodium form relative to the hydronium form, hence transport of sodium is preferred over transport of hydronium. Therefore, by minimizing transport of hydronium the wastage current is minimized and current efficiency improved.

Wastage current is minimized across the lower (suppressed) section of the suppressor (Rw) and good current efficiency is achieved as the eluent carries the bulk of the current in this device. For cation analysis membrane 34 has a strong base functionality and membrane 36 could have either a weak base functionality or a hydroxide selective base functionality. In both cases the wastage current is minimized.

Based on the foregoing, it is preferred to have the membrane with the higher net charge close to the ion source channel; for example, anode that generates hydronium in the case of anion analysis (and hydroxide in the case of cation analysis). The present suppressor has significantly less current wastage in the lower section.

In the above suppressor, neutral packing, low capacity packing, or high capacity packing may be eliminated in the sample stream flow channel. Conversely, it is preferred to use high capacity packing in the ion receiving flow channel and ion source flow channel.

In its above embodiment, the packing principle may also be employed. Thus, the ion receiving flow channel and ion source flow channel (if present) include high capacity packing with the sample stream flow channel including neutral or low capacity stream packing.

In another embodiment, not shown, increased resistance of the downstream portion is achieved by including means, coupled electrically in series with the lower portion for increasing electrical resistance of the downstream portion. One such means is the use of an electrical resistor in the downstream portion but not in the upstream portion or using one or more resistors such that the downstream portion has a higher resistance than the upstream portion.

The resistance R of a conductor is defined as $$R = \frac{\rho L}{A}$$

where $\rho$ is the resistivity of the conductor in ohm-cm

L is the length of the conductor in cm

A is the cross-sectional area of the conductor in $cm^2$.

Thus, the resistance is directly proportional to the length and inversely proportional to the cross-sectional area of the conductor. In the suppressor example, the cross-sectional area of the downstream section could be reduced to increase resistance. The increased resistance of the lower section forces the current to be carried by the eluent in the upper section of the eluent channel/suppressor and hence good current efficiency is achieved.

For example, if $R_e$ is the resistance of the eluent (unsuppressed) section of the suppressor and $R_w$ is the resistance of the region where the eluent is completely in the suppressed form (water in above example), then the total resistance $R_t$ $$Rt = \frac{1}{\left\{\frac{1}{Re} + \frac{1}{Rw}\right\}}$$

As $R_w$ increases, $R_t$ approaches $R_e$ and hence current efficiency is improved.

Another means of increasing the resistance of $R_w$ is by attaching a resistance in series with $R_w$. One way to accomplish this is to use two spacers (e.g., lightly functionalized screens such as lightly sulfonated screens) in series with the lower section of the suppressor but not in the upper section of the suppressor. Such an arrangement increases the resistance in the lower section of the suppressor and forces the current to pass through the upper section of the suppressor. A resistor in place of the spacers will also accomplish increased resistance of the lower section relative to the upper section of the suppressor.

In another embodiment, an additional pair of electrodes is employed. Thus, for a one-membrane device, one pair of electrodes is positioned in electrical communication with the upstream portion of the sample stream flow channel and ion receiving flow channel, respectively. The second pair of electrodes is positioned in the downstream portion of the same channels. Each of these electrode pairs is connected to an independent power source. Wastage current is minimized and current efficiency is improved by supplying a lower current to the downstream portion relative to the upstream portion. Thus, in use, the electrical current in the upstream portion exceeds the electrical current in the downstream portion. Suitable ratios are from 10:1 to 2:1. For a two-membrane device, the electrode pairs are disposed in the ion receiving flow channels and the ion source flow channel, respectively.

In another embodiment of current efficiency, the downstream portion of the sample stream flow channel in which the matrix ion is suppressed has a net charge of no greater than about 0.9 times, preferably no greater than about 0.3, and most preferably the net charge of the upstream is no greater than about 0.1. The packing in the sample stream flow channel could be altered in this preferred embodiment to have a higher resistance on the downstream portion relative to the upstream portion. By increasing the resistance in the downstream portion, less hydronium is wasted in the formation of water, hence current efficiency is improved. In a preferred embodiment a carboxylate functionalized eluent screen accomplishes the above. The carboxylate functionality in the hydronium form is highly resistive compared to the eluent form. Similarly, a partially functionalized screen with approximately the upper half of the screen in the functionalized form and the lower half in the neutral or lightly functionalized form would accomplish the above. For example, an eluent screen with full sulfonation on the upper half and room temperature sulfonation or no sulfonation in the lower half of the screen. Similarly, combinations of the above-discussed functionalities could be used to improve current efficiency.

In another embodiment of the invention, a constant voltage is applied from a constant voltage power source. The advantage of a constant voltage mode is that the current required for suppression would be self regulated or adjusted to the eluent strength or concentration. Hence, unlike constant current mode, which requires prior knowledge of the eluent strength or concentration, constant voltage would correct for variations in eluent strength caused by, for example, variations in the eluent flow rate.

In gradient applications, a constant voltage mode for current efficient suppressors would allow for self regulation of the current required for suppression. Under a constant current mode this would require setting the current to suppress the highest eluent concentration, hence under low eluent conditions (usually during the beginning of the run) high currents are imposed on the device. Higher currents result in higher heat and gas formation and, in turn, higher noise and baseline perturbations. These effects also limit the maximum operable concentration under constant current mode. Constant voltage mode overcomes the above limitation and the current is self adjusted during gradients, hence a higher concentration range could be suppressed.

Any of the foregoing methods and apparatus for increasing current efficiency can be used in combination with two or more approaches. Thus, for example, the packing principle can be used in combination with the two membranes of different net charge.

In order to illustrate the present invention, the following examples of its practice are provided.

EXAMPLE 1

In Example 1, a sandwich suppressor device, as illustrated in FIG. 2 suitable for anion analysis, is constructed for use in the system of FIG. 1.

The cation-exchange screens 41 and 43 are formed as follows. The base screen is of a polyethylene monofilament type supplied by Tetko, Inc. Such screen is immersed in a solution of 30% styrene w/w in methylene chloride solvent. Grafting occurs by irradiation with gamma rays at a dose of 10,000 rads/hour for about 48–120 hours at 80°–90° F. under nitrogen atmosphere. The screen is then soaked in 10% w/w chlorosulfonic acid in methylene chloride for 4 hours at about 40° C. The screen is then immersed in 1M KOH at 55° C. for 30 minutes.

The substrates for the ion exchange membranes 34 and 36 are film or sheet type made of PTFE (Teflon). The substrate polymer is solvent and acid or base resistant. Such film is first grafted with styrene monomer and then functionalized to form a cation-exchange membrane. Membrane functionalization, by sulfonation, is performed in the same manner as functionalizing the screens in the previous paragraph.

The gasket is formed of an inert, chemical resistant material suitable for providing a liquid seal for the flow channel it defines.

The overall hardware includes external support blocks made of a rigid nonconductive material (PEEK) serving to house the screens, membranes and electrodes. It also provides structural support for the suppressor. The top has four fittings (one pair for the eluent inlet and eluent outlet and other pair for regenerant inlet and regenerant outlet, respectively). The blocks are pressed together by conventional means, such as screws, to obtain a liquid-tight seal.

The sub-assemblies are formed as follows. A screen with surrounding gasket material is formed by cutting a gasket from plastic film that includes the desired flow path and pressing this gasket into the screen such that only the flow path is not covered by the gasket material. For each gasket, two rectangles of ultra-low molecular weight polyethylene (Parafilm "M", American National Can Company) are cut with the appropriate dimensions of the flow channel also cut out. The screen is sandwiched between the Parafilm gaskets, and the stack is pressed to 10,000–20,000 psi at ambient temperature. One eluent screen/gasket assembly and two regenerant ones made with sulfonated screen and Parafilm are required per suppressor. The screen mesh (the size of the screen opening) for the central screen 32 are 140 $\mu$m for the outside screens 41 and 43.

Two rectangles of cation-exchange membrane are cut to match the inlets and outlets of the flow path profile and the overall dimension of the screens. 3 mil thick polytetrafluorethylene (Teflon) base membrane is used.

An anode and a cathode made of conductive, chemically platinum foil, 0.025 mm thick (Johnson Matthey Electronics), with measurements of 1.0 by 12.0 cm were used.

The system is in the form of a chromatographic column arranged in series with the suppressor. The solution leaving the column is directed to the suppressor wherein the electrolyte is converted to a weakly conducting form. The effluent was then directed to a detector in the form of a flow-through conductivity cell for detecting all the resolved ionic species. The effluent after passing through the conductivity cell is redirected to the inlet port of the outside channels in which the detector cell effluent is electrolyzed supplying hydronium ions ($H^+$) for neutralization reaction.

The suppressor used was a commercially available Dionex 4 mm ASRS which was modified by removing the functionalized screens 32 in the sample stream flow channel and replacing it with a neutral polyethylene screen.

A direct current power supply from Pharmacia was used in the constant current mode. The suppressor was tested for current efficiency by pumping in 25, 50, 100 and 200 mM sodium hydroxide solutions at a flow rate of 1 ml/min. The conductivity of the effluent from the suppressor was monitored using a conductivity cell. The current applied to the suppressor was varied over a range of 5–20 mA near the current efficient regime and the background level of the effluent was monitored. Good suppression occurred, with the device showing the lowest resistance and lowest background (average background conductance was approximately 2.35 $\mu$Siemens/cm in the range of 25–200 mM of sodium hydroxide) near the current efficient-regime. When the current applied was plotted against the eluent concentration, excellent fit was observed as shown in FIG. 9. A slope of 0.61 mM/mA was obtained, which is very close to the faradaic value of 0.62 mM/mA.

EXAMPLE 2

Anion Separations Using a Current Efficient Suppressor-constant Current Mode

The suppressor was similar to the one described in Example 1. A direct current power supply from Pharmacia was used in the constant current mode. The analytical column was a Dionex AS4A-SC (4×250 mm) column and the eluent used was 1.8 mM sodium carbonate/1.7 mM sodium bicarbonate at a flow rate of 2 ml/min. Excellent separation and detection of a test mixture comprising 7 anions was achieved at an applied current of 18 mA, 3 V, as shown in FIG. 10. Peaks labeled 1–7 are Fluoride, Chloride, Nitrite, Bromide, Nitrate, Phosphate and Sulfate. A background level of 15–16 $\mu$S/cm indicated complete suppression of the eluent to carbonic acid using the neutral screen suppressor.

EXAMPLE 3

Anion Separations Using a Current Efficient Suppressor-constant Voltage Mode

A direct current power supply from Hoeffer Scientific was used in the constant voltage mode. The suppressor used was a commercially available Dionex 2 mm ASRS device that was modified by removing the functionalized eluent screen and replacing it with a neutral polyethylene screen as shown schematically in FIG. 2. All other conditions were similar to Example 2. The analytical column was a Dionex AS11 (4×250 mm) column and the eluent used was 10 mM sodium hydroxide at a flow rate of 1 ml/min. Excellent separation and detection of a test mixture comprising 4 anions was achieved at an applied voltage of 7 V as shown in FIG. 11. Peaks labeled 1–4 are Fluoride, Chloride, Sulfate and Nitrate. The current generated was approximately 16 mA, which is very close to the theoretical faradaic current of 16 mA.

EXAMPLE 4

Anion Separations Using a Current Efficient Suppressor-constant Voltage Mode

A direct current power supply from Hoeffer Scientific was used in the constant voltage mode. All other conditions were similar to Example 2. The analytical column was a Dionex AS10 (4×250 mm) column and the eluent used was 85 mM sodium hydroxide at a flow rate of 1 ml/min. Excellent separation and detection of a test mixture comprising 4 anions was achieved at an applied voltage of 7 V as shown in FIG. 12. Peaks labeled 1–4 are Fluoride, Chloride, Sulfate and Nitrate. The current generated was approximately 137 mA which is very close to the theoretical current.

EXAMPLE 5

Anion Separations Using a 10.5-V Battery

A DC power source of 10.5 V was made by arranging 7 1.5 V cells in series. All other conditions were similar to Example 3. A sample comprising 3 anions were well resolved as shown in FIG. 13. Peaks labeled 1–3 are Fluoride, Chloride and Sulfate.

EXAMPLE 6
Gradient Separations Using a Current Efficient Suppressor Powered by a Universal AC-DC Adapter A universal AC-DC adapter set at 10.5 V DC was used to power the suppressor, all other conditions are similar to Example 3. The eluents used were E1: 50 mM NaOH and E2: 200 mM NaOH. The gradient used was 100% E1 at 0 min to 38% E1, 62% E2 at 31 min. The advantage of constant voltage is that the current is adjusted by the influx of the gradient. Hence, the current is self-regulating in the eluent channel. In contrast to the above approach, constant-current devices supply a huge excess of current (particularly at the beginning of the gradient), which may translate at noise and heat and be detrimental to the device lifetime. Separation of a text mixture comprising 5 anions is shown in FIG. 14. Peaks labeled 1–5 are Fluoride, Chloride, Sulfate, Phosphate and Nitrate. No trap column was used in this and the increase in the background is attributed to increasing levels of carbonate in the eluent.

EXAMPLE 7
Cation Separations Using a Current Efficient Suppressor

A direct current power supply from Hoeffer Scientific was used in the constant-voltage mode. The suppressor used was a commercially available Dionex 4 mm CSRS device that was modified by removing the functionalized eluent screen and replacing it with a neutral polyethylene screen as shown schematically in FIGS. 1–4. All other conditions were similar to Example 2. The analytical column was a Dionex CS12A (4×250 mm) column and the eluent used was 18 mM methanesulfonic acid (MSA) at a flow rate of 1 ml/min. Good separation and detection of a test mixture comprising 4 cations was achieved at an applied voltage of 5 V as shown in FIG. 15. The current generated was 29 mA, which is indistinguishable from the theoretical value of 29 mA. Peaks labeled 1–4 are Lithium, Sodium, Ammonium and Potassium.

EXAMPLE 8

Recovery Studies on an Oligonucleotide Standard

A commercially available Dionex 2 mm ASRS device was compared with the suppressor of Example 3. The positions marked as A and B are positions marked on the ASRS as eluent in and eluent out. Similarly, positions C and D are regenerant in and out. Both suppressors were operated under external water mode. A direct current power supply from Pharmacia was used in the constant-current mode. Recovery of a target oligonucleotide a $(GT)_{10}$20-mer, was attempted using both suppressors. The eluent used was sodium salt of triflouro acetic acid (Gradient: 0.13 M–0.35 M) with and without added acetonitrile (16%). The results of the recovery studies, shown in Table 1, clearly show the advantage of having a neutral screen instead of a functionalized screen.

TABLE 1

Recovery studies ASRS-Cation exchange eluent vs. Neutral eluent screen

| Eluent screen-Functionality | Acetonitrile (% v/v) | % Recovery |
|---|---|---|
| Cation exchange | 0 | 84 |
| Neutral | 0 | 94 |

TABLE 1-continued

Recovery studies ASRS-Cation exchange eluent vs. Neutral eluent screen

| Eluent screen-Functionality | Acetonitrile (% v/v) | % Recovery |
|---|---|---|
| Cation exchange | 16 | 91 |
| Neutral | 16 | 103 |

EXAMPLE 9
Cations in Acid Analysis

The device of Example 7 is used as a sample preparation device useful in analyzing cations in acid. The conductive acid component is reduced to the suppressed low or non-conducting form (from HCl to water) and the sample cations converted to their base form (from NaCl to NaOH). The sample ions could be diverted to a preconcentrator and then analyzed using an IC system and a suppressor of Example 7. The above is a current-efficient suppressor for sample preparation application.

EXAMPLE 10
Anions in Base Analysis

The device of Example 2 is used as a sample preparation device useful in analyzing anions in base. The conductive base component is reduced to the suppressed low or non-conducting form (from NaOH to water) and the sample anions are converted to their acid form (from NaCl to HCl). The sample ions could be diverted to a preconcentrator and then analyzed using an IC system and a suppressor of Example 2. The above is a current-efficient suppressor for sample preparation applications.

EXAMPLE 11
Low Capacity Functionalized Eluent Screen

The device was similar to Example 1 except the eluent screen was replaced with a functionalized screen which had a very low capacity. The base screen is made of polyethylene monofilament type supplied by Tetko, Inc. This screen is immersed in a solution of 30% styrene w/w in methylene chloride solvent. Grafting occurs by irradiation with gamma rays at a dose of 10,000 rads/hour for about 48–120 hours at 80–90° F. under nitrogen atmosphere. The screen is functionalized by soaking in concentrated sulfuric acid for 1 hour at room temperature. Then the screen was washed with dilute acid followed by base and water, and then fitted in place of the neutral screen. The capacity of this screen was measured to be 0.005 meq/g. The above suppressor was tested using a Dionex AS10 column and 100 mM sodium hydroxide eluent under external water mode. DI water was pumped at a flow rate of 3 mL/min through the electrode chambers while eluent was flowing through the sample stream channel at 1 mL/min. Excellent separation of a test mixture comprising of 5 anions was achieved at an applied voltage of 5V as shown in FIG. 16. Peaks labeled 1–6 corresponding to Fluoride, Carbonate, Chloride, Sulfate, Phosphate and Nitrate. The typical noise in this chromatogram was less than 3 nS $cm^{-1}$. The current generated was 169 mA, which is approximately 95% current-efficient. There is some wastage of the current in the formation of water by transport of hydronium ion across the eluent channel. However, most of the current in this device is still carried by the eluent.

What is claimed is:

1. A method for treating an aqueous sample stream including analyte ions of one charge and matrix ions of opposite charge to said analyte ions, said method comprising flowing the sample stream through a sample stream flow channel simultaneously flowing an aqueous stream through an ion receiving flow channel separated therefrom by a first ion exchange membrane capable of passing only ions of opposite charge to said analyte ions, while passing a current between said sample stream flow channel and said ion receiving flow channel to reduce the concentration of said matrix ions in an effluent from said sample stream flow channel, said sample stream flow channel having an upstream sample stream portion containing said matrix ions and an adjacent downstream sample stream portion in which said matrix ions have been suppressed, said upstream portion having an electrical resistance no greater than about 0.9 times that of the downstream portion, said ion receiving flow channel including stationary flow-through first packing of ion exchange material of the same charge as said first membrane.

2. A method for treating an aqueous sample stream including analyte ions and matrix ions of opposite charge to said analyte ions, said method comprising flowing said aqueous sample stream through a sample stream flow channel, simultaneously flowing an aqueous stream through an ion receiving flow channel separated from said sample stream flow channel by an adjacent first ion exchange membrane capable of passing only ions of opposite charge to said analyte ions, flowing an aqueous stream through an ion source flow channel on the opposite side of said sample stream flow channel from said ion receiving channel, said ion source flow channel being separated from said sample stream flow channel by a second ion exchange membrane, said first membrane having a net charge of no greater than about 0.9 times the net charge of said second membrane, while passing a current between first and second electrodes in electrical communication with said ion source flow channel and ion receiving stream flow channel, respectively, to reduce the concentration of said matrix ions in an effluent from said sample stream flow channel.

3. A method for treating an aqueous sample stream including analyte ions and matrix ions of opposite charge to said analyte ions, said method comprising flowing said aqueous sample stream through a sample stream flow channel, simultaneously flowing an aqueous stream through an ion receiving flow channel separated from said sample stream flow channel by a first ion exchange membrane capable of passing only ions of opposite charge to said analyte ions, said ion exchange membrane having an upstream portion substantially in the matrix ion form and a downstream portion where the matrix ion is substantially reduced said downstream portion having a net charge of no greater than about 0.9 times the net charge of the upstream portion, while passing a current between first and second electrodes in electrical communication with said sample stream flow channel and ion receiving flow channel, respectively, to reduce the concentration of said matrix ions in an effluent from said sample stream flow channel.

4. A method of treating an aqueous stream including analyte ions of one charge and matrix ions of opposite charge to said analyte ions, said method comprising flowing the sample stream through a sample stream flow channel, simultaneously flowing an aqueous stream through an ion receiving flow channel separated therefrom by a first ion exchange membrane capable of passing only ions of opposite charge to said analyte ions, said sample stream flow channel having an upstream sample stream portion containing matrix ions and an adjacent downstream sample stream portion in which said matrix ions have been suppressed, passing current at a first amperage between said upstream sample stream portion and an adjacent upstream ion receiving stream portion using first and second electrodes, and passing a second current at a second lower amperage between said downstream sample stream portion and an adjacent downstream ion receiving stream portion using third and fourth electrodes.

5. The method of claims 2, 3, or 4 further comprising stationary flow-through first packing in said ion receiving flow channel.

6. The method of claims 1, 2, or 3 in which said current is maintained at a substantially constant voltage along the length of said sample stream flow channel.

7. The method of claims 1, 2, 3, or 4 further comprising detecting said analyte ions exiting from said sample stream flow channel.

8. The method of claim 7 in which after detecting, a portion of the sample stream is recycled to said ion receiving stream flow channel.

9. The method of claim 7 in which after detecting, a portion of the sample stream is recycled to said ion source flow channel.

10. The method of claim 7 used for ion chromatography in which said analyte ions in said sample stream are chromatographically separated prior to flowing the same through said ion receiving flow channel.

11. The method of claims 1, 2, 3 or 4 used for pretreating a sample prior to analysis, said method further comprising detecting said analyte ions exiting from said sample stream flow channel.

12. The method of claim 11 further comprising separating said analyte ions exiting from said sample stream flow channel.

13. The method of claims 1 or 4 further comprising flowing an ion source aqueous stream through an aqueous stream ion source channel separated from said sample stream flow channel by a second ion exchange membrane capable of passing only ions of opposite charge to said analyte ions of interest, said current passing from said ion source flow channel through said sample stream flow channel to said ion receiving flow channel.

14. The method of claim 13 in which neutral second packing is disposed in said sample stream flow channel.

15. The method of claim 13 in which second ion exchange packing is disposed in said sample stream flow channel, said second packing having a total ion exchange capacity no greater than about 0.9 times the total ion exchange capacity of said first ion exchange packing.

16. The method of claim 1 in which neutral second packing is disposed in said sample stream flow channel.

17. The method of claim 1 in which second ion exchange packing is disposed in said sample stream flow channel, said second packing having a total ion exchange capacity no greater than about 0.9 times the total ion exchange capacity of said first ion exchange packing.

* * * * *

UNITED STATES PATENT AND TRADEMARK OFFICE
CERTIFICATE OF CORRECTION

PATENT NO.     : 6,077,434
DATED          : June 20, 2000
INVENTOR(S)    : Kannan Srinivasan et al.

It is certified that error appears in the above-identified patent and that said Letters Patent is hereby corrected as shown below:

<u>Title page,</u>
Item [75], Inventors, correct the spelling of "Neboisa Avdalovic" to
-- Nebojsa Avdalovic --.

<u>Column 15,</u>
Line 11, change "± 10 mA" to -- +/-10 mA --.

Signed and Sealed this

Eighth Day of April, 2003

JAMES E. ROGAN
*Director of the United States Patent and Trademark Office*